(12) United States Patent
Overes et al.

(10) Patent No.: US 10,420,649 B2
(45) Date of Patent: Sep. 24, 2019

(54) ARTIFICIAL JOINT IMPLANT (71) Applicant: 41 Hemiverse AG, Bettlach (CH)

(72) Inventors: Tom Overes, Langendorf (CH); Robert Frigg, Bettlach (CH)

(73) Assignee: 41 Hemiverse AG, Bettlach (CH)

( * ) Notice: Subject to any disclaimer, the term of this patent is extended or adjusted under 35 U.S.C. 154(b) by 8 days.

(21) Appl. No.: 15/565,456

(22) PCT Filed: Apr. 15, 2015

(86) PCT No.: PCT/CH2015/000058
§ 371 (c)(1),
(2) Date: Oct. 10, 2017

(87) PCT Pub. No.: WO2016/165030
PCT Pub. Date: Oct. 20, 2016

(65) Prior Publication Data
US 2018/0116808 A1 May 3, 2018

(51) Int. Cl.
A61F 2/40 (2006.01)
A61F 2/30 (2006.01)
(Continued)

(52) U.S. Cl.
CPC .............. A61F 2/3854 (2013.01); A61F 2/32 (2013.01); A61F 2/40 (2013.01); A61F 2/4014 (2013.01);
(Continued)

(58) Field of Classification Search
CPC ........ A61F 2/40; A61F 2/4014; A61F 2/4081; A61F 2/32; A61F 2/34; A61F 2/36; A61F 2/30028; A61F 2002/30225; A61F 2002/30332; A61F 2002/30649; A61F 2002/30242; A61F 2002/3065; A61F 2002/30652; A61F 2002/30654;
(Continued)

(56) References Cited

U.S. PATENT DOCUMENTS 3,837,008 A    9/1974  Bahler et al.
3,886,601 A *  6/1975  Findlay ................. A61F 2/3854
                                                 446/104

(Continued)

FOREIGN PATENT DOCUMENTS

WO    2010105073 A1    9/2010

Primary Examiner — Alvin J Stewart
(74) Attorney, Agent, or Firm — Rankin, Hill & Clark LLP (57) ABSTRACT An artificial joint implant (1) comprising a first element (2) with a socket (4) and a second element (3) with a ball head (5), wherein said ball head (5) is insertable in said socket (4) such as to form a ball-and-socket connection between said first element (2) and said second element (3), and the movement of said ball head (5) in said socket (4) is restricted by means of a protrusion (6.1; 6.2) engaged in a groove (7), whereby said protrusion (6.1; 6.2) has a central axis A2 and is protruding from the surface of said socket (4) and said groove (7) is provided on the surface of said ball head (5) or vice versa; —said groove (7) is positioned along a great circle of said ball head (5) or of said socket (4), —said protrusion (6.1; 6.2) has a shape allowing rotation of the protrusion around its central axis A2 when received in the groove (7); and—the surface roughness of the protrusion (6.1; 6.2) and/or of the groove (7) is at most 25 micrometers.

37 Claims, 6 Drawing Sheets (51) Int. Cl.
  *A61F 2/38* (2006.01)
  *A61F 2/32* (2006.01)
  *A61F 2/42* (2006.01)
  *A61F 2/36* (2006.01)
(52) U.S. Cl.
  CPC .............. *A61F 2/4081* (2013.01); *A61F 2/42* (2013.01); *A61F 2/30767* (2013.01); *A61F 2002/30028* (2013.01); *A61F 2002/30225* (2013.01); *A61F 2002/30332* (2013.01); *A61F 2002/30364* (2013.01); *A61F 2002/30367* (2013.01); *A61F 2002/30616* (2013.01); *A61F 2002/30635* (2013.01); *A61F 2002/30662* (2013.01); *A61F 2002/30663* (2013.01); *A61F 2002/30932* (2013.01); *A61F 2002/30937* (2013.01); *A61F 2002/3617* (2013.01); *A61F 2002/4018* (2013.01); *A61F 2002/4022* (2013.01); *A61F 2002/4029* (2013.01); *A61F 2002/4085* (2013.01); *A61F 2002/4088* (2013.01); *A61F 2002/4096* (2013.01)
(58) Field of Classification Search
  CPC ...... A61F 2002/30662; A61F 2002/665; A61F 2002/4018; A61F 2002/4022; A61F 2/4241; A61F 2/4261
  See application file for complete search history.

(56) References Cited

U.S. PATENT DOCUMENTS

| | | | | |
|---|---|---|---|---|
| 4,003,096 A | | 1/1977 | Frey | |
| 4,040,130 A | * | 8/1977 | Laure | A61F 2/4261 623/21.13 |
| 4,106,128 A | * | 8/1978 | Greenwald | A61F 2/3804 623/21.13 |
| 4,279,041 A | * | 7/1981 | Buchholz | A61F 2/32 403/123 |
| 4,642,123 A | * | 2/1987 | Noiles | A61F 2/32 623/22.2 |
| 4,950,299 A | * | 8/1990 | Noiles | A61F 2/32 623/22.18 |
| 4,960,427 A | * | 10/1990 | Noiles | A61F 2/32 623/22.18 |
| 4,978,356 A | * | 12/1990 | Noiles | A61F 2/32 623/23.4 |
| 5,007,932 A | * | 4/1991 | Bekki | A61F 2/4241 623/23.39 |
| 5,405,399 A | * | 4/1995 | Tornier | A61F 2/4241 623/21.15 |
| 5,938,700 A | * | 8/1999 | Lippincott, III | A61F 2/4241 623/21.15 |
| 6,383,223 B1 | * | 5/2002 | Baehler | A61F 2/4241 623/16.11 |
| 6,454,808 B1 | * | 9/2002 | Masada | A61F 2/4241 623/21.13 |
| 6,682,565 B1 | * | 1/2004 | Krishnan | A61F 2/4241 623/21.16 |
| 7,108,720 B2 | * | 9/2006 | Hanes | A61F 2/32 623/22.11 |
| 8,771,366 B2 | * | 7/2014 | Whitaker | A61F 2/32 623/22.11 |
| 9,649,194 B2 | * | 5/2017 | Forsell | A61F 2/3609 |
| 9,925,053 B2 | * | 3/2018 | Overes | A61F 2/40 |
| 9,999,513 B2 | * | 6/2018 | Overes | A61F 2/40 |
| 2002/0143402 A1 | * | 10/2002 | Steinberg | A61F 2/30742 623/22.16 |
| 2003/0233146 A1 | * | 12/2003 | Grinberg | A61F 2/4425 623/17.14 |
| 2007/0055378 A1 | * | 3/2007 | Ankney | A61B 17/1671 623/17.15 |
| 2010/0179661 A1 | * | 7/2010 | Berelsman | A61F 2/38 623/20.12 |
| 2010/0256770 A1 | * | 10/2010 | Hakansson | A61F 2/4241 623/21.16 |
| 2012/0004733 A1 | * | 1/2012 | Hodorek | A61F 2/40 623/19.11 |
| 2016/0235539 A1 | * | 8/2016 | Overes | A61F 2/40 |
| 2016/0256288 A1 | * | 9/2016 | Overes | A61F 2/40 |
| 2018/0116808 A1 | * | 5/2018 | Overes | A61F 2/40 |

* cited by examiner

ARTIFICIAL JOINT IMPLANT

The invention relates to an artificial joint implant according to the preamble of claim 1.

Many different types of implants for artificial joints are known in the prior art. Specifically, joint implants having a ball-and-socket type are used for hip and shoulder implants. However, implants of the ball-and-socket type may also be used in condyloid joints, such as the radiocarpal joint of the wrist, metacarpophalangeal joints of the hand and metatarsophalangeal joints of the foot.

In certain types of implants, notably the radiocarpal, metacarpophalangeal and metatarsophalangeal joints at least one degree of freedom of movement of a ball- and socket joint has to be restricted such as to mimic the function of the natural joint. Further, in certain circumstances, it may also be beneficial to limit the degree of freedom of movement of a ball-and-socket joint in artificial hip or shoulder implants.

From WO 2010 1050 73 EXACTACH a motion inducing reverse shoulder assembly. A motion inducing element on the glenoid component is interacting with a humeral liner on the humeral component so that it abuts with a stop defined by a pocket. The document does not further define the positions of the interacting structures and it appears that various paths of movement of the motion inducing element are possible rendering the function of the joint unpredictable.

From US 2002/0143402 STEINBERG a hip joint prosthesis is known where the femoral head is provided with a rail and the acetabulum with a channel in order to limit movement of the joint. Since the cuboid rail is kept in the channel having the same geometry the rail—together with the ball head—is not able to rotate in the channel thereby excluding an important degree of freedom.

This document discloses only rails (=protrusions) which have trapezoidal cross section and channels (=grooves) with a matching cross-section so that the relative movement of the two joint components is mainly a rotation about one single axis for each of the two rail/channel combinations (disregarding the relatively small lateral movement due to the slight oversize of the channel in regard of the rail).

It is the object of the invention to create a joint implant which allows limiting a movement of a ball-and-socket connection in at least one degree of freedom, providing a low wear mechanism to replace joints with two, four and 6 articulation directions, namely:

In applications for replacement of saddle joints such as an elbow joint, the joint implant provides two combined axes of rotation, providing 4 major articulation directions. In applications for hinge joints the joint implant provides two combined axes of rotation, wherein the joint implant provides 2 major articulation directions but also provides means of guided play to compensate for inaccuracies in the motion. For ball in socket joints such as the shoulder and hip, the joint implant provides two combined axes of rotation, providing the first 4 major articulation directions of needed 6 articulation directions, and can be combined with an element providing a third axis of rotation, facilitating the remaining 2 major articulation directions, wherein the axes of rotation not necessarily intersect.

The solution of the invention is specified by the features of claim 1.

The joint according to the invention provides two axes of rotation, which allow rotation around each axis, but also combinations of these two axes, comparable to a joystick. The motion is not guided or blocked.

Movement of said ball head in said socket is restricted in at least one degree of freedom by means of at least one protrusion engaged in at least one groove. Thereby, said at least one protrusion is provided on said socket and said at least one groove is provided on said ball head or vice versa.

By provision of a protrusion and a groove a very simple yet effective restriction of the freedom of movement of the ball-and-socket connection is realized. Further, the inventive joint implant is very simple to assemble and features no additional parts which need to be fastened to the bones of a patient, hence allowing a quick and simple implantation in a patient. Further, ball-and-socket connections have a high congruency and exhibit excellent wear characteristics. Therefore, the same freedom of motion as a joint including two hinge axes with much better wear characteristics and less parts is achieved.

The first element and the second element may be shaped and sized according to the intended use of the joint implant. For example, the inventive joint implant may be used for hip replacement. In this case the first element may be formed as hemispherical acetabular cup. Accordingly, the second element featuring the ball head is formed as femoral component to be inserted in a patient's femur. Various embodiments of artificial acetabular cups and femoral components are known to a person having skill in the art.

Further, as a second non-binding example, the joint implant according to the present invention may be used for shoulder replacement. In this case, the first element is shaped as a glenoid disc to be inserted into the glenoid cavity of a patient. Accordingly, the second element is provided in the form of a humeral shaft to be inserted in the patient's humerus.

The present invention is not restricted to a specific shape, size or type of said first and said second element but may rather be used in connection with various different types of artificial joints. For example, a joint implant according to the present invention may also be used to replace an elbow, knee, radiocarpal joint, metacarpophalangeal joint or metatarsophalangeal joint. In each of these exemplary uses, the first and the second element are shaped and sized to be implanted in the corresponding anatomical location of a patient.

Ball-and-socket type connections are known to a person having skill in the art. Basically, a ball head shaped portion is inserted in a corresponding socket. Usually, a ball-and-socket type connection allows the ball head to rotate around three different axes within said socket. I.e. the ball head has three rotational degrees of freedom to move relative to the socket. Preferably, the socket is sized such that the ball head snugly fits within the socket, hence only allowing rotational movements of the ball head within the socket. However, in certain circumstances, the socket may be shaped such as to allow a limited translation of the ball head within the socket. In such a circumstance, the ball head will of course have more degrees of freedom. E.g. if translation is allowed in one direction for a limited distance, the ball head will have one translational degree of freedom and three rotational degrees of freedom, totaling four degrees of freedom.

The term "degree of freedom" as used in the present application is understood to encompass rotational movement around an axis of rotation as well as a translational movement along a line of travel.

By having an engagement of the at least one protrusion within the at least one groove the ball head is restricted from making a movement in a direction which would urge the protrusion out of the groove. Hence, only movements which allow the protrusion to move within the groove remain possible. The groove may therefore be considered a kind of guide way for the movements of the ball head within the socket.

The protrusion may be provided in the ball head. Hence, the groove will be provided in the socket. Alternatively, the protrusion may be located in the socket. In this case the groove is located in the ball head. As long as at least one protrusion engaged in at least one groove is provided, it is irrelevant whether the at least one groove or the at least one protrusion is located in said socket or in said ball head.

Preferably, the first element and/or the second element are provided as monobloc structures which preferably include surfaces enhanced for bone ingrowth, e.g. by application of a coating.

Preferably, said at least one groove is positioned along a great circle of said ball head or said socket. Provision of the groove along a great circle allows limiting the movement of the ball head within the socket along a first rotational axis intersecting the centre of the socket. However, as the at least one protrusion may glide along and rotate within said at least one groove, rotation about the two remaining axes of rotation, which are both orthogonal to said first rotational axis remains possible for said ball-and-socket connection.

Preferably, said at least one groove has a width which is equal to or larger than a width of said at least one protrusion. This allows the at least one protrusion to rotate and slide within said at least one groove.

In a preferred embodiment, the width of said at least one groove is larger than the width of said at least one protrusion. Hence, the movement of the ball head in the at least one restricted degree of freedom is still possible, albeit only in a limited manner. This allows providing a joint implant having full motion capacity in all degrees of freedom except in the restricted degree of freedom, where only a limited range of motion is available. For example, this may allow for a limited "wobbling-type" motion, i.e. a motion with play in the restricted degree of freedom, for example to reduce the incidence of damage to the joint or surrounding tissue when an external force is exerted in the direction of the restricted degree of freedom.

Preferably, said at least one groove is provided on said socket and spans only a portion of the distance between the edge and the apex of said socket. Hence, movement of the at least one protrusion may be partially restricted in a second degree of freedom. This allows providing a joint implant where the motion of the ball-and-socket connection between the first element and the second element mimics a natural joint including any movement constraints. E.g. the joint implant may be provided such that the rotation of the ball head within the socket around one axis may be restricted to different maximal rotational angles depending on the direction of the rotation.

Preferably, said ball head is in the form of a dome or of a spherical segment. As such forms present at least one substantially flat portion, the second element may be provided in a great variety of shapes. Further, the substantially flat portion may comprise anchoring points for further implant components. This e.g. allows to use the inventive joint implant in a modular system, where a patient specific adaptation of the implant is made possible by providing different sizes of components attachable to the second element, such as for example stems of different lengths or diameters.

Preferably, said at least one groove is provided on said ball head, wherein said at least one groove spans only a portion of the distance between a circumferential edge and the apex of said dome or only a portion between two circumferential edges of said spherical segment.

In this way, movement of the at least one protrusion may be partially restricted in a second degree of freedom in the case where the at least one groove is arranged on the ball head.

Preferably, said first element further comprises an inlay rotatably coupled to a base portion around a first axis of rotation, wherein said at least one protrusion and said at least one groove are arranged to block at least a rotational movement of said ball-and-socket connection in a second axis of rotation which is essentially parallel to said first axis of rotation.

Such a configuration allows offsetting the centre of rotation around said first axis. Preferably, the socket is located on an eccentric position on said inlay. Further, the socket may also be spaced from said inlay by means of a shaft or stem. Hence, different variations of the offset of the centre of rotation may be realized.

Preferably, the at least one protrusion has a central axis which is oriented such as to intersect the centre of the socket or ball-head, i.e. the at least one protrusion points towards said centre.

Further, the ball-head is preferably locked within the socket such as to avoid any disassembly of the ball- and socket joint. This locking is preferably enabled by a form-fit engagement of the ball-head within the socket, e.g. by providing an opening to the socket which is smaller than the dimension of the ball-head once inserted and oriented in the correct direction. For example, the ball-head may be configured as dome having a defined largest circumference and a defined height. Typically, the largest circumference corresponds to the circumference of a great circle of the ball head. The socket is configured to feature an opening having dimensions which are larger than the height of the ball-head but smaller than the largest circumference.

Therefore, the ball-head may only be inserted transversally into said socket. After a re-orientation of the ball head, the disassembly of the ball-and-socket connection is prevented since the largest circumference of the ball-head does not fit through the opening of the socket.

A suitable material for the ball head, the offset adaptor and the base member is CoCr. For the Inlay HDPE is preferred.

The Polyethlene inlay preferably rotates within the base member (corresponding to the glenoid ring in a shoulder prosthesis) to prevent from friction against the bone upon rotation.

Alternative metals are Titanium, Titanium alloys, Stainless steel, or combinations there-off. The inlay can also be of PEEK. Other materials are ceramic materials. With ceramics a Ceramic on Ceramic articulation is possible. For reduction of wear on metal on metal combinations, Diamond Like Coatings can be used.

Purposefully the surface roughness is at most 5 micrometers and preferably at most 0.8 micrometers. Surface roughness Ra may be measured in two ways: contact and non-contact methods. Contact methods involve dragging a measurement stylus across the surface; these instruments are called profilometers.

Non-contact methods include: interferometry, confocal microscopy, focus variation, structured light, electrical capacitance, electron microscopy, and photogrammetry.

In a special embodiment the protrusion is circular-cylindrical, circular-conical or spherical. Such a shape allows unhindered longitudinal movement of the protrusion as well as unhindered rotation around the central axis of the protrusion within said groove.

In a further embodiment special embodiment said protrusion has a central axis which is oriented such as to intersect the centre of the socket or the ball-head and forming an axis A2.

Preferably said protrusion is integral with the ball head (5), respectively with the socket.

Purposefully said protrusion has a height of maximum 40%, and preferably maximum 20% of the diameter of the ball head, respectively of the socket. Said protrusion may have a maximum diameter at its base of 75%, preferably of maximum 50% of the diameter of the ball head, respectively of the socket.

In a special embodiment said socket is at least hemispherical.

In a special embodiment said groove (7) has a width which is equal to or larger than a maximum diameter of said protrusion (6.1, 6.2). The width of the groove purposefully is between 100% and 125% of the maximum width of the protrusion, preferably between 100% and 105% of the maximum width of the protrusion.

In a further embodiment the width of the groove is between 100.005% and 100,100% of the maximum width of the protrusion, and preferably between 100.01 and 100.05. With these tolerances there is the advantage of reduction of friction and prevention pf point loading which otherwise would cause delamination of the polyethylene material of the socket.

Preferably the cross-section of the groove is a half circle or less. The bottom of the groove may be essentially flat. In a further embodiment said groove is provided on the surface of said socket, and spans only a portion of the distance between a circumferential edge and an apex of said socket.

In a further embodiment said ball head is in the form of a dome or of a spherical segment. Said groove may be provided on said ball head, and said groove spans only a portion of the distance between a circumferential edge and an apex of said dome or only a portion between two circumferential edges of said spherical segment.

In a special embodiment the artificial joint implant is provided with two protrusions which are positioned diametrically to each other, enabling the ball head to rotate around two different axes when the ball head is inserted into the socket with the two protrusions located in the groove, namely (i) around an axis A2 passing through the two protrusions; and
(ii) around an axis A3 orthogonal to a plane defined by the great circle along which the groove extends and orthogonal to axis A2; but
preventing rotation of the socket around an axis A1 orthogonal to both axis A2 and A3.

There are several advantages of having two protrusions, namely: (i) easier introduction of the ball head into the socket; (ii) higher stability of the ball and socket joint; (iii) reduction of wear, (iv) reduction of friction and stresses, (v) guarantee that at least one protrusion is always engaged within the groove wherein engagement means that never two central axis of the protrusions are outside of the groove; and (vi) the ball-head with two protrusions is compliant to motions along two axes or combined motion along these tow axis. These motions result in zero mechanical moments in the joint.

The two protrusions may have a different shape. In cases where the joint needs to be designed asymmetrically because of impingement with anatomical structures, it would be possible to have a small protrusion and a large protrusion. In case for example of an intervertebral disc replacement, that needs to be placed more posterior on the vertebral body, a small posterior and a large anterior protrusion could be provided.

The depth of the groove is purposefully at most 400%, preferably at most 200% of the height of the protrusion. The length of the groove may be at least 200%, preferably at least 400% of the depth of the groove.

In a special embodiment the relation $A_G/A_S$ between area $A_G$ of the groove measured on the fictional hemispherical surface and the total area $A_S$ of the socket is in the range of 1:40 and 1:10, preferably in the range of 1:30 and 1:15.

In another embodiment the relation $A_B/A_S$ between the base area $A_B$ of the protrusion measured at its base on the fictional hemispherical surface and the total area $A_S$ of the socket is at most 1:55, preferably at most 20:1. Purposefully the relation $A_B/A_S$ is in the range of 1:17 and 1:11.5 and preferably in the range of 1:14 and 1:12.

In a special embodiment of the he artificial joint implant said first element further comprises an inlay rotatably coupled to a base portion around a fourth axis of rotation (A4), wherein said protrusion and said groove are arranged to block at least a degree of freedom of said ball-and-socket connection around a first axis of rotation (A1) which is essentially parallel to the fourth first axis (A4) of rotation.

In a special embodiment the plane which is defined by the groove (i.e. the plane in which the groove is curved) is essentially orthogonal or parallel to the virtual line connecting the center of the socket with the center of the inlay.

The distance between the first axis of rotation (A1) and the fourth axis of rotation (A4) can be in the range of 3 mm to 20 mm, preferably 5 mm to 15 mm.

In a special embodiment the ball head is attached or connectable to a prosthesis stem having a symmetry plane (i.e. the plane in which the stem is curved).

In further a special embodiment the artificial joint implant is designed as a shoulder endo-joint prosthesis and the groove has purposefully a length of at least 150°, preferably at least 180°. The artificial joint implant designed as shoulder prosthesis allows 20° adduction, 80° abduction, 75° internal & external rotation, and 360° anteversion & retroversion.

This shoulder prosthesis is especially useful for the treatment of failed reverse shoulder prosthesis.

The artificial joint prosthesis according to the invention provides the biomechanical advantages of the reverse shoulder prosthesis by medialisation and lateralisation of the centre of rotation initiating compensation for a deficient supra-spinatus muscle by increased activation of the deltoideus muscle.

A further advantage of this artificial joint prosthesis is that there is no necessity for an intact glenoid bone. After a failed reverse prosthesis the glenoid bone is very compromised but still the artificial joint prosthesis according to the invention can be implanted.

This prosthesis also provides advantages for younger patients, because the glenoid bone does not need to be prepared at all. Other advantages are that normally the preparation of the glenoid bone is the trickiest for the good outcome, takes most time during surgery, and is technically demanding. All this falls away: Better results with less experienced surgeons, less blood loss, less surgery length (narcosis).

Furthermore the system can be made adaptable to most convertible prosthesis systems; by changing of the articulation mechanism, the bone integrated stem does not need to be removed.

In further a special embodiment the artificial joint implant is designed as an ankle joint prosthesis and the groove has purposefully a length of at least 5°, preferably at least 100.

In further a special embodiment the artificial joint implant is designed as a wrist prosthesis.

In further a special embodiment the artificial joint implant is designed as spinal disc prosthesis.

In a further embodiment the ball head and the protrusion are an integral monolith component. The protrusion may have has a fixed position with regard to ball head.

In a further embodiment the plane which is defined by the groove is parallel or perpendicular with regard to the symmetry plane going through the central axis of the prosthesis stem.

The invention comprises also a method of manufacture of the artificial joint according to the invention which is characterized in that the ball head and the protrusion are turned from the solid to obtain a one-piece ball head.

Other advantageous embodiments and combinations of features come out from the detailed description below and the totality of the claims.

BRIEF DESCRIPTION OF THE DRAWINGS

The drawings used to explain the embodiments show.

In the figures, the same components are given the same reference symbols.

Figure 1:
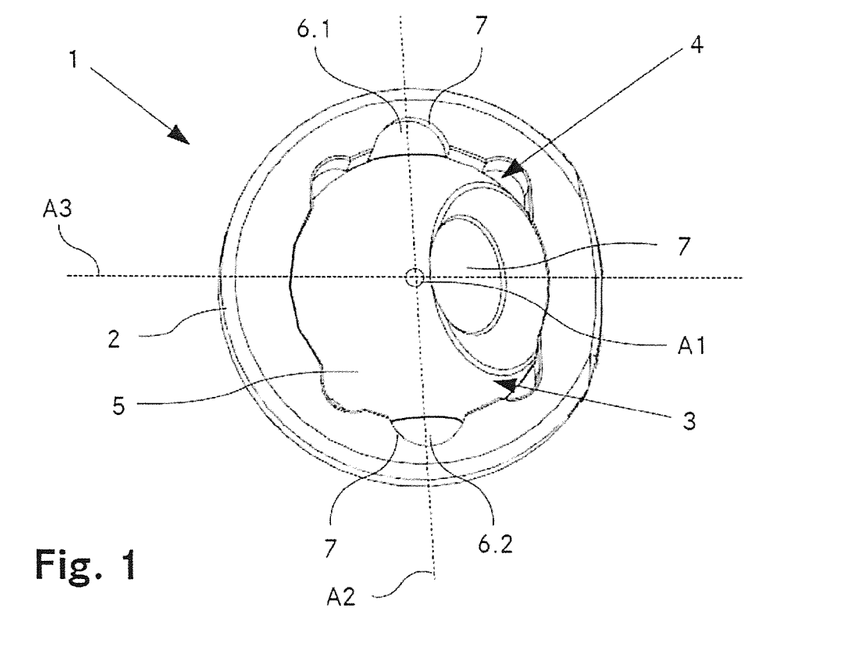
FIG. 1 An exemplary joint implant according to the present invention.

FIG. 1 shows an exemplary joint implant 1 according to the present invention. The joint implant 1 comprises a first element 2 with a hemispherical socket 4. Further, the joint 10 implant 1 comprises a second element 3 including a ball head 5. The ball head 5 is arranged within the socket 4 thus forming a ball-and-socket connection.

In the exemplary embodiment shown, the second element 3 comprises the ball head 5 as well as a connection portion 20 in the form of a hole, e.g. including a thread. Alternatively, the connection portion 20 may be configured as morse taper. Further components, such as a shaft or stem may be connected with the second element 3 by means of the connection portion 20. In the shown embodiment the ball head 5 is provided in the form of a dome.

The hemispherical socket 4 includes a groove 7 into which two protrusions 6.1, 6.2 provided on said ball head 5 are engaged. The groove 7 as well as the protrusions 6.1, 6.2 have a matching hemispherical shape. Without provision of the groove 7 and the protrusions 6.1, 6.2 the ball head 3 would be able to rotate freely around three axes of rotation A1, A2, A3 within the socket. It has to be noted that a first axis A1 is oriented parallel to the viewing direction when looking at the figure. However, the engagement of the two protrusions 6.1, 6.2 into the groove 7 restricts rotational movement of the ball head 3 around the first axis A1, as the two protrusions 6.1, 6.2 are form-fittingly engaged within the groove 7. Hence, the two protrusions 6.1, 6.2 engaged within the groove 7 results in a movement restriction of the joint implant 1 in one degree of freedom. In the shown embodiment, the groove 7 has the same shape and width as the two protrusions 6.1, 6.2, hence any movement around the first rotation axis A1 is prevented. Alternatively, the groove 7 may have a width which is slightly larger than the width of the two protrusions 6.1, 6.2. With such an alternative embodiment, the ball head 3 would be able to carry out small movements around the first axis of rotation A1, hence enabling a limited "wobbling" of the ball head 3 within the socket 4 around the third axis of rotation A1.

Rotational movement of the ball head 3 around a third axis of rotation A3 is enabled by a sliding motion of the two protrusions 6.1, 6.2 within the groove 7 and rotational movement around a second axis of rotation A2 by a rotation of the two protrusions 6.1, 6.2 within the groove 7.

Figure 2:
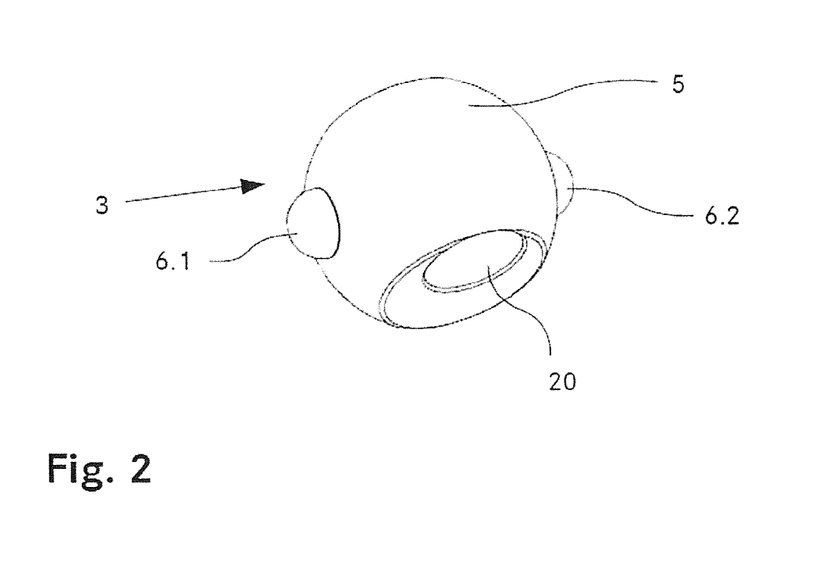
FIG. 2 a detailed view of the second element of the joint implant according to FIG. 1.

FIG. 2 shows a detailed view of the second element 3 of the joint implant 1 according to FIG. 1. The shape of the two protrusions 6.1, 6.2 as well as of the ball head may be clearly recognized in this figure. As may be seen, the ball head 5 is in the shape of a dome, i.e. of a sphere which is cut by a plane, while the two protrusions 6.1, 6.2 are in the form of hemispheres.

Figure 3:
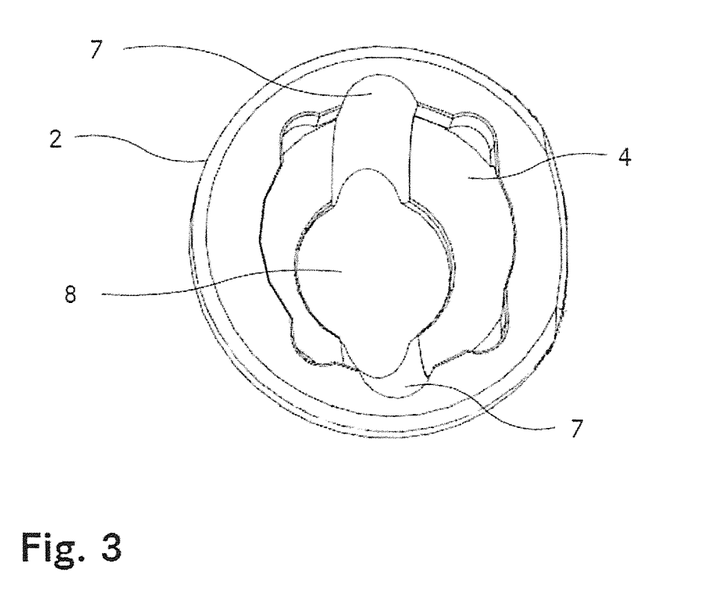
FIG. 3 a detailed view of the first element of the joint implant according to FIG. 1.

FIG. 3 shows a detailed view of the first element 2 of the joint implant 1 according to FIG. 1. As may be seen, the groove 7 has a hemispherical shape and is arranged on the hemispherical socket 4 along a great circle. The groove 7 thereby spans the socket 4 from edge to edge. Around the apex of the hemispherical socket 4, an opening 8 is provided.

Figure 4:
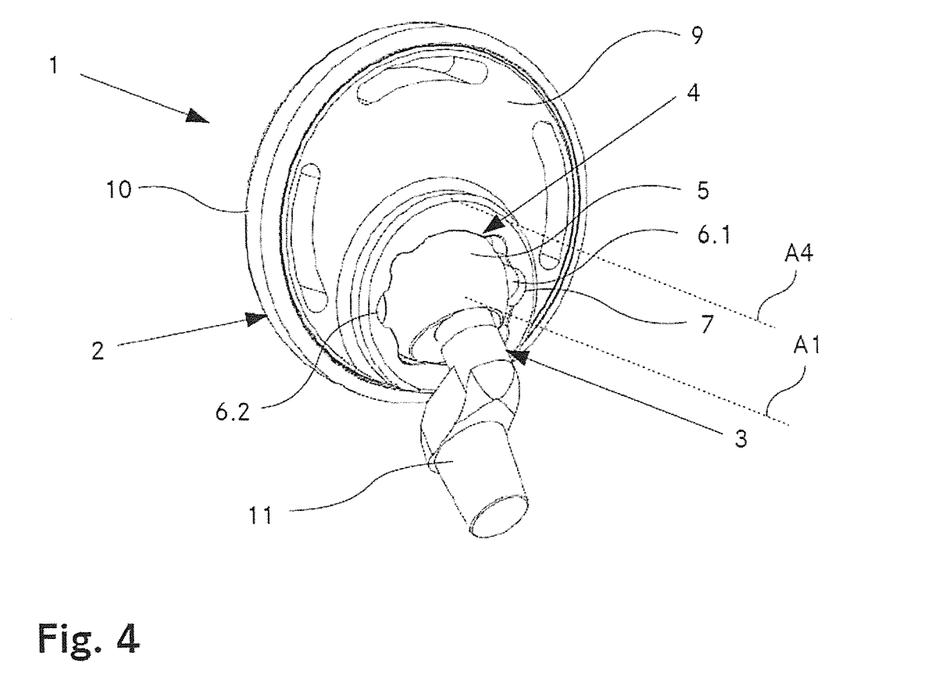
FIG. 4 an alternative embodiment of a joint implant according to the present invention.

FIG. 4 shows an alternative embodiment of a joint implant 1 according to FIG. 1. This embodiment may be used e.g. as shoulder prosthesis. The first element 2 comprises a circular inlay 9 on which the hemispherical socket 4 is located at an eccentric position. The inlay 9 is rotatably connected to a base member 10 and rotates around a fourth axis A4. The groove 7 of socket 4 is arranged in such a way that the first axis A1 around which rotational movement is prohibited by the engagement of the two protrusions 6.1, 6.2 and the groove 7 is arranged generally parallel to the fourth rotational axis A4 of the inlay 9. Hence, by the specific arrangement of the embodiment according to FIG. 4, an offset of the third rotational axis A3 is achieved. Further, the second element 3 comprises a generally Z-shaped adaptor 11 connected with the ball head 5. By means of the adaptor 11 it is possible to offset the attachment of a shaft or stem to the second element. Such an offset is particularly advantageous in connection with a shoulder prosthesis.

Figure 5:
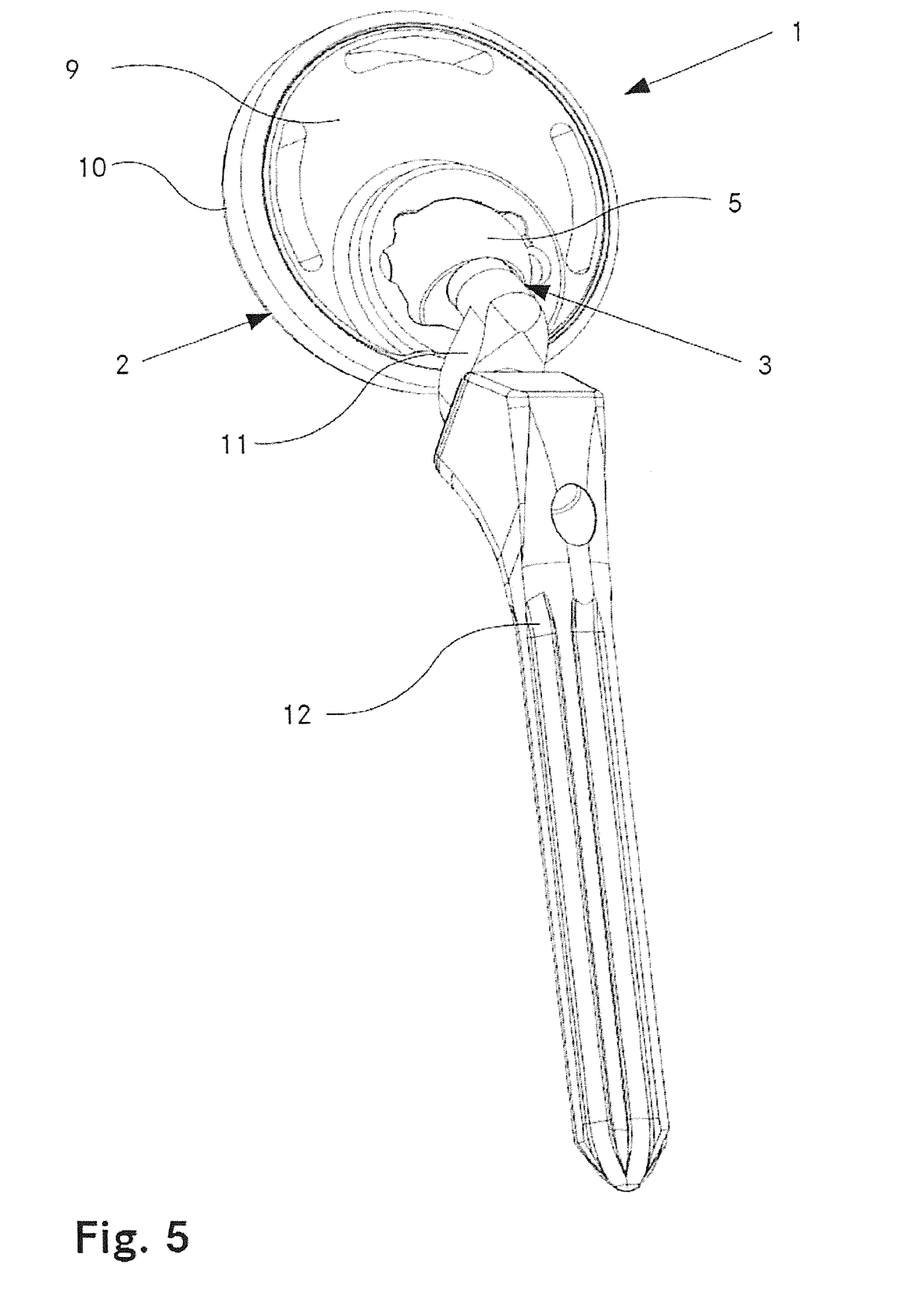
FIG. 5 the joint implant according to FIG. 4 configured as shoulder prosthesis.
Figure 6:
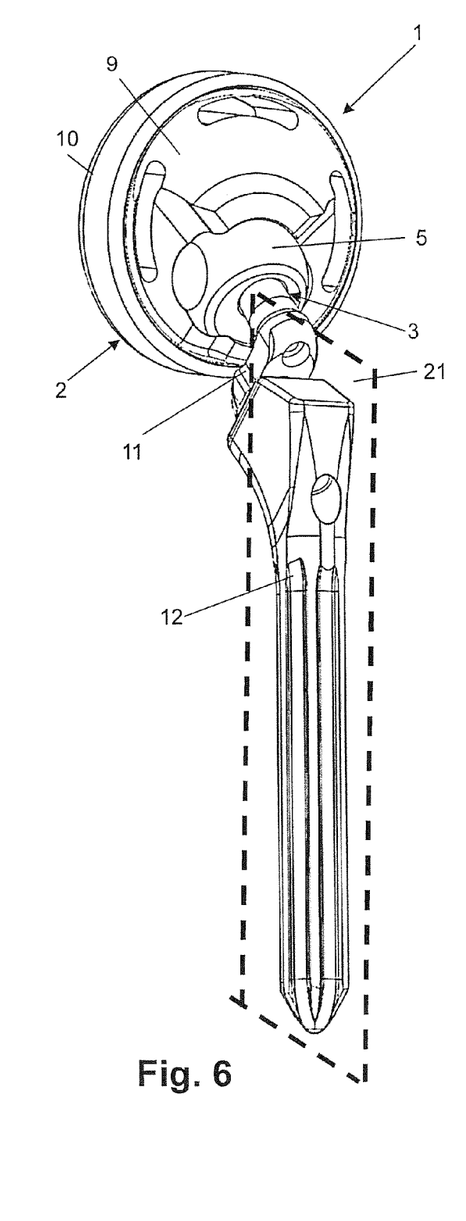
FIG. 6 a perspective view of the joint implant of FIG. 5.
Figure 7:
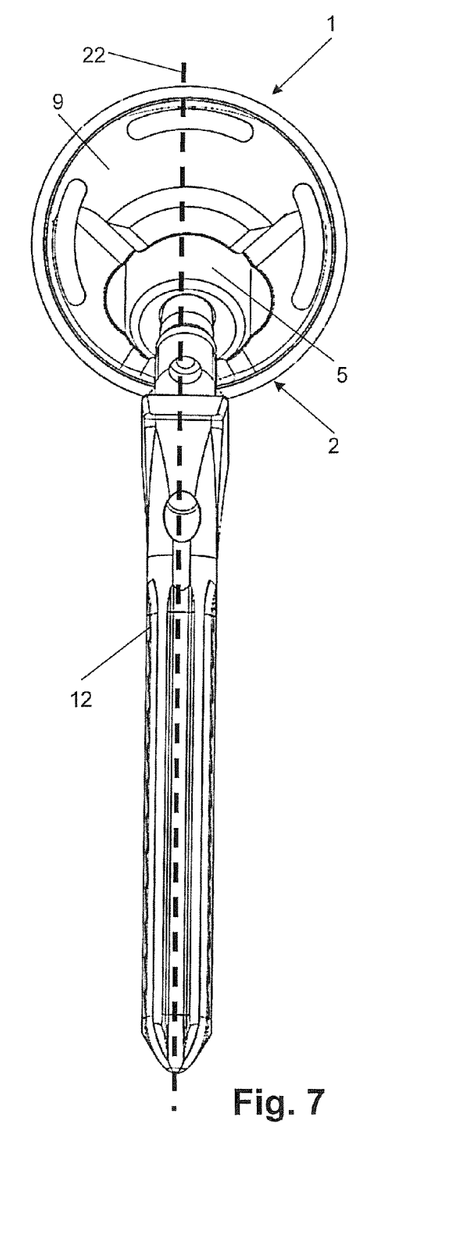
FIG. 7 a detailed view from lateral of the joint implant of FIG. 5.

FIGS. 5 to 7 show the joint implant 1 according to FIG. 4 configured as shoulder prosthesis. A prosthesis stem 12 is affixed to the adaptor 11. The stem 12 is sized and shaped to be inserted in a humerus of a patient. The ball head 5 is coupled to the prosthesis stem 12 via the adaptor 11 so that the plane which is defined by the groove 7 (FIG. 4) is perpendicular with regard to the symmetry plane 21 (FIG. 6) going through the central axis 22 (FIG. 7) of the prosthesis stem 12. In an alternative embodiment the ball head 5 may be arranged with respect to the prosthesis stem 12 in such a way that the plane which is defined by the groove 7 is parallel with regard to the symmetry plane 21 going through the central axis 22 of the prosthesis stem 12. The base element 10 is preferably sized and shaped to be positioned in the glenoid cavity, its outer rim engaging with the coracoid and acromial processes. Provision of a set of adaptors 11 having different configurations enables the customization of the shoulder prosthesis implant to the anatomy of different patients in a simple manner.

Figure 8:
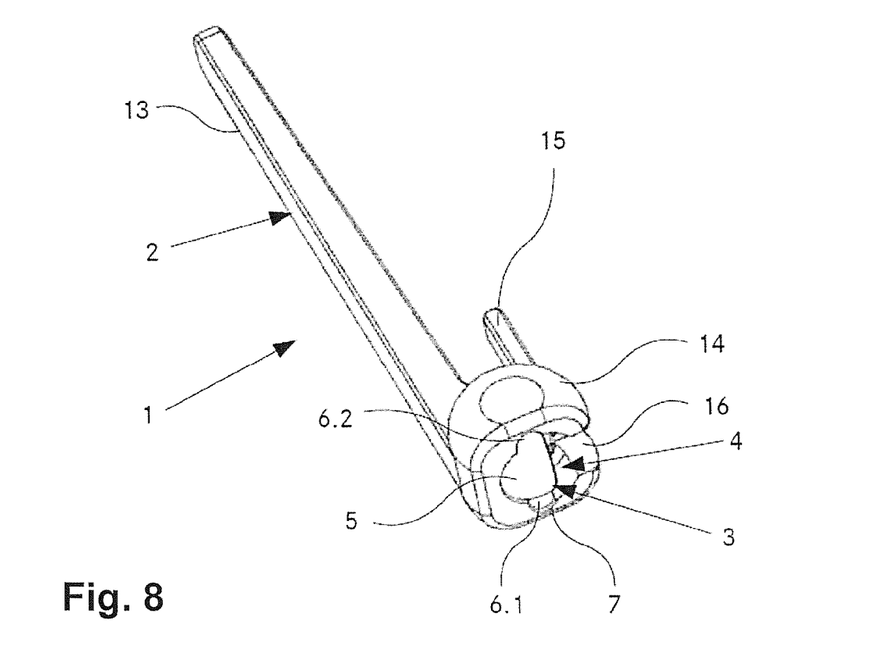
FIG. 8 an inventive joint implant configured as artificial elbow.

FIG. 8 shows the inventive joint implant 1 configured as artificial elbow. The first element 2 comprises a stem 13 sized and shaped to be implanted in the distal humerus of a patient as well as a generically hemispherical head portion 14 comprising the socket 4. An anterior support member 15 extends from the head portion 14 parallel to the stem 13, said anterior support member 15 only spanning along a short portion of the stem 13 and being intended to engage with the anterior cortex of a humeral bone. The head portion 14 includes a recess 16 intersecting the socket 4. The ball head 5 of the second element 3 of the joint implant 1 is inserted into the socket 4, whereby the groove 7 and the two protrusions 6.1, 6.2 restrict the movement of the ball head 5 within the socket 4 such that the stem 13 and an ulnar stem (shown in FIG. 9) inserted into the connection portion 20 of the second element 3 may not be moved relative to each other outside of a plane parallel to the longitudinal axis of the stem 13. This configuration allows providing a joint implant which mimics the natural freedom of movement of an elbow joint.

Figure 9:
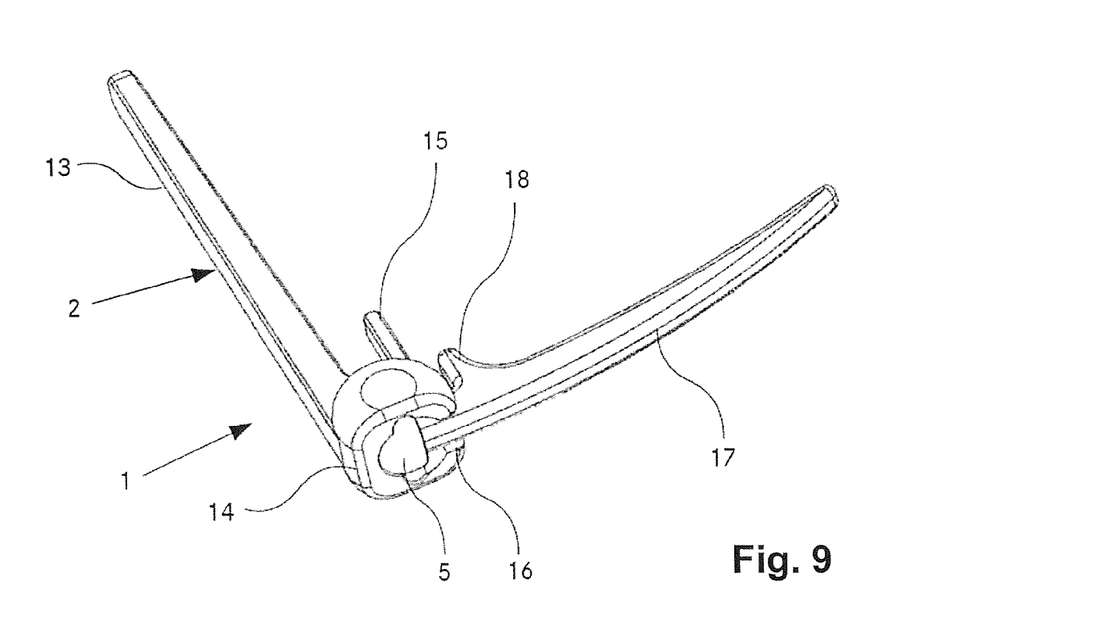
FIG. 9 the complete artificial elbow according to FIG. 8.

The complete artificial elbow is represented in FIG. 9. In addition to the elements as shown in FIG. 8, an ulnar stem 17 is attached to the ball head 5. The function of the recess 16 becomes apparent as allowing an enhanced range of motion to the ulnar stem 17 in one direction corresponding to a flexion movement of the elbow as opposed to the other direction. An additional depth stop 18 is arranged on the ulnar stem 17 which serves to limit the depth of insertion of the stem 17 into an ulnar bone.

Figure 10:
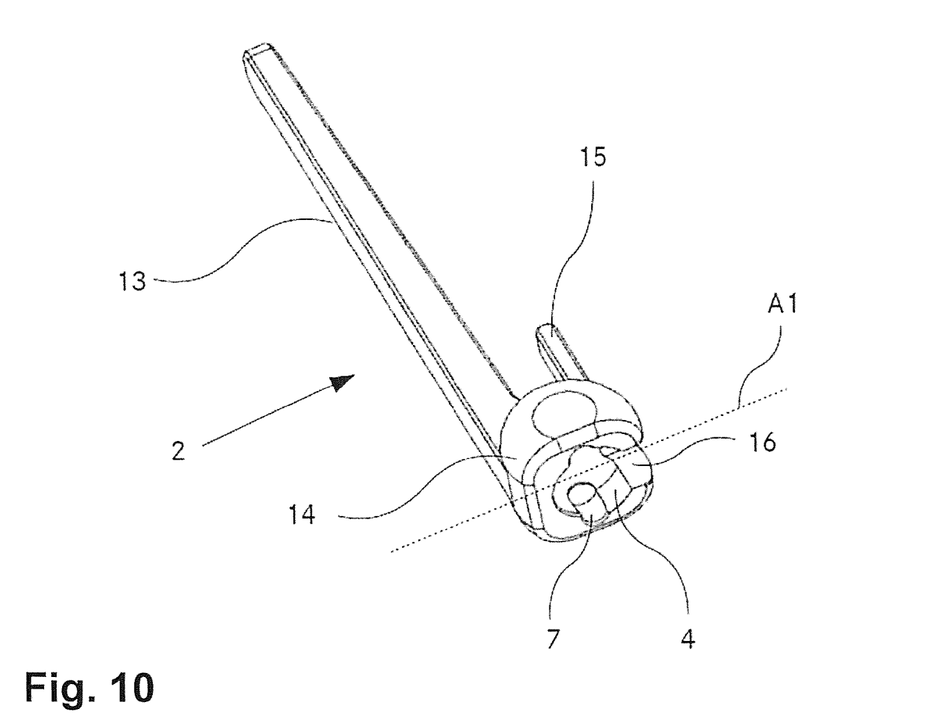
FIG. 10 the first element of the artificial elbow according to FIG. 9.

FIG. 10 shows the first element 2 of the artificial elbow in some more detail. As may be seen, the groove 7 does not span from the edge of the socket 4 to the apex, but terminates at about half the distance between the edge and the apex. This allows to additionally limiting the rotational movement of the ball head 5 within the socket 4 around the first axis A1.

Figure 11:
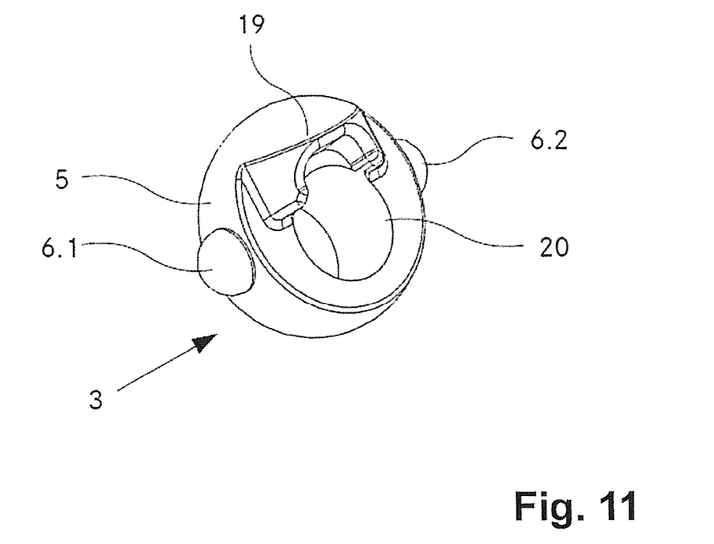
FIG. 11 the second element of the artificial elbow according to FIG. 9.

The second element 3 of the artificial elbow is shown in FIG. 11. As in the previous examples, the ball head 5 is in the shape of a dome. However, in this embodiment, the ball head 5 comprises a nose 19 protruding from the otherwise hemispherical shape. The nose 19 acts as an additional support for the ulnar stem 17 which may be attached to the ball head 5 by means of connection portion 20.

The invention claimed is:

1. An artificial joint implant comprising:
a first element with a socket; and
a second element with a ball head;
wherein said ball head is insertable in said socket such as to form a ball-and-socket connection between said first element and said second element,
wherein movement of said ball head in said socket is restricted by a protrusion engaged in a groove,
wherein said protrusion has a central axis A2,
wherein said protrusion protrudes from a surface of said socket and said groove is provided on a surface of said ball head or said protrusion protrudes from the surface of said ball head and said groove is provided on the surface of said socket, and
wherein:
a) said groove is positioned along the circumference of a great circle of said ball head or of said socket,
b) said protrusion has a shape allowing rotation of the protrusion around its central axis A2 when received in the groove; and
c) a surface roughness of the protrusion and/or of the groove is at most 25 micrometers.

2. The artificial joint implant according to claim 1, wherein the surface roughness is at most 5 micrometers.

3. The artificial joint implant according to claim 1, wherein said protrusion has a shape selected from the group consisting of circular-cylindrical, circular-conical and spherical.

4. The artificial joint implant according to claim 1, wherein the central axis A2 of the protrusion is oriented such that it intersects a center of the socket or the ball-head.

5. The artificial joint implant according to claim 1, wherein said protrusion is integral with the ball head or with the socket from which it protrudes.

6. The artificial joint implant according to claim 1, wherein said protrusion has a height that is a maximum of 40% of a diameter of the ball head or a diameter of the socket from which it protrudes.

7. The artificial joint implant according to claim 1, wherein said protrusion has a maximum diameter at its base of 75% of the diameter of the ball head or of the socket from which it protrudes.

8. The artificial joint implant according to claim 1, wherein said socket comprises at least a portion that is hemispherical.

9. The artificial joint implant according to claim 1, wherein said groove has a width that is greater than or equal to a maximum diameter of said protrusion.

10. The artificial joint implant according to claim 9, wherein the width of the groove is between 100% and 125% of the maximum width of the protrusion.

11. The artificial joint implant according to claim 10, wherein the width of the groove is between 100.005% and 100.1% of the maximum width of the protrusion.

12. The artificial joint implant according to claim 1, wherein a cross-section of the groove defines a half circle or an arc that is less than a half circle.

13. The artificial joint implant according to claim 1, wherein a bottom of the groove is flat.

14. The artificial joint implant according to claim 1, wherein said groove is provided on the surface of said socket, and wherein said groove spans only a portion of a distance between a circumferential edge and an apex of said socket.

15. The artificial joint implant according to claim 1, wherein said ball head is in a form of a dome or of a spherical segment.

16. The artificial joint implant according to claim 15, wherein said groove is provided on said ball head, and wherein said groove spans only a portion of a distance between a circumferential edge and an apex of said dome or only a portion between two circumferential edges of said spherical segment.

17. The artificial joint implant according to claim 1, wherein the artificial joint implant is provided with two protrusions, which are positioned diametrically to each other so as to the ball head to rotate around two different axes when the ball head is inserted into the socket with the two protrusions located in the groove, namely:
around an axis A2 passing through the two protrusions; and
(ii) around an axis A3 orthogonal to a plane defined by a great circle along which the groove extends and orthogonal to axis A2; and wherein two protrusions prevent rotation of the socket around an axis A1 orthogonal to both axis A2 and A3.

18. The artificial joint implant according to claim 17, wherein the two protrusions each have a different shape.

19. The artificial joint implant according to claim 1, wherein a depth of the groove is at most 400% of a height of the protrusion.

20. The artificial joint implant according to claim 1, wherein a length of the groove is at least 200% of a depth of the groove.

21. The artificial joint implant according to claim 1, wherein a relation $A_G/A_S$ between area $A_G$ of the groove measured on a hemispherical surface and a total area $A_S$ of the socket is in the range of 1:40 and 1:10.

22. The artificial joint implant according to claim 21, wherein a relation $A_B/A_S$ between a base area $A_B$ of the protrusion measured at its base on the hemispherical surface and the total area $A_S$ of the socket is at most 1:55.

23. The artificial joint implant according to claim 22, wherein the relation $A_B/A_S$ is in a range of 1:17 and 1:11.5.

24. The artificial joint implant according to claim 1, wherein said first element further comprises an inlay rotatably coupled to a base portion around a fourth axis of rotation, wherein said protrusion and said groove are arranged to block at least a degree of freedom of said ball-and-socket connection around a first axis of rotation which is essentially parallel to the fourth axis of rotation.

25. The artificial joint implant according to claim 24, wherein a plane defined by the groove is orthogonal or parallel to a virtual line connecting a center of the socket with a center of the inlay.

26. The artificial joint implant according to claim 24, wherein a distance between the first axis of rotation and the fourth axis of rotation is in a range of 3 mm to 20 mm.

27. The artificial joint implant according to claim 1, wherein the ball head is attached or connectable to a prosthesis stem with a symmetry plane.

28. The artificial joint implant according to claim 27, wherein a plane defined by the groove is parallel to or perpendicular to the symmetry plane going through the central axis of the prosthesis stem.

29. The artificial joint implant according to claim 1, wherein the artificial joint implant is a shoulder endo-joint prosthesis and the groove has a length of at least 150°.

30. The artificial joint implant according to claim 29, wherein the artificial joint implant allows at least 20° adduction, at least 80° abduction, at least 75° internal & external rotation, and 360° anteversion and retroversion.

31. The artificial joint implant according to according to claim 1, wherein the artificial joint implant is an ankle joint prosthesis and the groove has length of at least 5°.

32. The artificial joint implant according to according to claim 1, wherein the artificial joint implant is a wrist prosthesis.

33. The artificial joint implant as in one of claims 1-27, in which the artificial joint implant is a spinal disc prosthesis.

34. The artificial joint implant according to claim 1, wherein the ball head and the protrusion are an integral monolith component.

35. The artificial joint implant according to claim 1, wherein the protrusion has a fixed position with respect to the ball head.

36. A method for manufacturing an artificial joint according to claim 1 comprising turning the ball head and the protrusion from a solid to obtain a one-piece ball head.

37. A method for treating a failed reverse shoulder prosthesis in a patient comprising implanting an artificial joint implant according to claim 1 in the patient's shoulder.

* * * * *

UNITED STATES PATENT AND TRADEMARK OFFICE
CERTIFICATE OF CORRECTION

PATENT NO.        : 10,420,649 B2                                 Page 1 of 1
APPLICATION NO.   : 15/565456
DATED             : September 24, 2019
INVENTOR(S)       : Tom Overes et al.

It is certified that error appears in the above-identified patent and that said Letters Patent is hereby corrected as shown below:

On the Title Page

Items (71) Applicant and (73) Assignee, delete --"41 Hemiverse AG"-- add "41Hemiverse AG"

In the Claims

In Column 10, Line 63, add --"(i)"-- before "around an axis A2 passing through the two protrusions;"

In Column 12, Line 15, delete the first --"according to"-- after the word "implant"

Signed and Sealed this
Thirty-first Day of December, 2019

Andrei Iancu
*Director of the United States Patent and Trademark Office*